United States Patent [19]
Cohen et al.

[11] Patent Number: 5,808,026
[45] Date of Patent: Sep. 15, 1998

[54] SEQUENCE OF AF1Q CDNA

[75] Inventors: Amos Cohen, Thornhill; William Tse; Weimin Zhu, both of Toronto, all of Canada

[73] Assignee: HSC Research and Development, Limited Partnership, Ontario, Canada

[21] Appl. No.: 589,080

[22] Filed: Jan. 23, 1996

[30] Foreign Application Priority Data

Jan. 26, 1995 [GB] United Kingdom .................... 9501386

[51] Int. Cl.$^6$ ........................... C07H 21/02; C07H 21/04
[52] U.S. Cl. .......................................... 536/23.1; 536/22.1
[58] Field of Search ................................ 536/23.1, 23.5, 536/24.31

[56] References Cited

FOREIGN PATENT DOCUMENTS 951386A 1/1995 Canada .

OTHER PUBLICATIONS

Tse et al, Blood 85(3):650–6, 1995.
Croce, C.M., "Role of Chromosome Translocations in Human Neoplasia", Cell 49:155–6, 1987.
Gauwerky, C.E. et al, "Chromosomal Translocations in Leukaemia", Semin Cancer Biol 4:333–40, 1993.
Kearney, L. et al, "Chromosome 11q23 Translocations in Both Infant and Adult Acute Leukemias Are Detected by in Situ Hybridization With a Yeast Artificial Chromosome", Blood 80:1659–65, 1992.
Petkovic, I. et al, "Cytogenetic Analysis in Children with Acute Nonlymphocytic Leukemia", Cancer Genet Cytogenet 58:155–9, 1992.
Young, B.D., "Cytogenetic and Molecular Analysis of Chromosome 11q23 Abnormalities In Leukaemia", Baillieres Clin Haematol 5:881–95, 1992.
Peu Ching–Hon, C.W.M. et al, "Biology and Clinical Significance of Cytogenetic Abnormalities in Childhood Acute Lymphoblastic Leukemia", Blood 76:1449–1463, 1990.
Heim, S.M., Cancer Cytogenetics 1987.
Djabali, M. et al, "A Trithorax–Like Gene is Interrupted by Chromosome 11q23 Translocations in Acute Leukaemias", Nat Genet 2:113–8, 1992.
Gu, Y et al, The t(4;11) "Chromosome Translocation of Human Acute Leukemias Fuses the ALL–1 Gene, Related to Drosophila Trithorax, to the AF–4 Gene", Cell 71:701–8, 1992.
Tkachuk, D.C. et al, "Involvement of a Homolog of Drosophila Trithorax by 11q23 Chromosomal Translocations in Acute Leukemias", Cell 71:691–700, 1992.

Harris, B.N. et al, "Involvement of a Homolog of Drosophila Trithorax by 11q23 Chromosomal Translocations in Acute Leukemias", Cell 71:691–700, 1992.
Harris, B.N. et al, "Variant Translocations (9;11): Identification of the Critical Genetic Rearrangement", Cancer Genet. 30:171–175, 1988.
Ma, Q. et al, "Analysis of the Murine All–1 Gene Reveals Conserved Domains with Human ALL–1 and Identifies a Motif Shared with DNA Methyltransferases", Proc. Natl Acad Sci U.S.A. 90:6350–4, 1993.
Gu, Y. et al, "E: Sequence Analysis of the Breakpoint Cluster Region in the ALL–1 Gene Involved in Acute Leukemia", Cancer Res 54:2326–30, 1994.
Hildren, J.M., "Heterogeneity in MLL/AF–4 Fusion Messenger RNA Detected by the Polymerase Chain Reaction in t(4;11) Acute Leukemia", Cancer Res 53:3853–6, 1993.
Thirman, M.J. et al, "Rearrangement of the MLL Gene in Acute Lymphoblastic and Acute Myeloid Leukemias with 11q22 Chromosomal Translocation", N Engl J Med 329:909–14, 1993.
Domer P. et al, "Acute Mixed–Lineage Leukemia t(4;11) (q21;q23) Generates an MLL–AF4 Fusion Product", Proc. Natl. Acad. Sci. USA 90:7884–7888, 1993.
Bernard, O.A., et al, "A Novel Gene, AF–Ip, Fused to HRX in t(1;11) (p32;q23), is Not Related to AF–4, AF–9 nor ENL", Oncogene 9:1039–45, 1994.
Prasad, R. et al, "Leucine–Zipper Dimerization Motif Encoded by the AF17 Gene Fused to ALL–1 (MLL) in Acute Leukemia", Proc. Natl. Acad. Sci. USA 91:8107–8111, 1994.
Schichman, S.A. et al, "All–1 Partial Duplication in Acute Leukemia", Proc. natl. Acad. Sci. USA 91:6236–6239, 1994.
McCabe, N.R. et al, "Cloning of cDNAs of the MLL Gene that Detect DNA Rearrangements and Altered RNA Transcripts in Human Leukemic Cells with 11q23 Translocations", Proc. Natl. Acad. Sci. USA 89:11794–8, 1992.
Wilson, T. et al, Nature 336–396–399, 1988.
Raimondi, S.C. et al, "Childhood Acute Lymphoblastic Leukemia with Chromosomal Breakpoints at 11q23", Blood 73:1627–34, 1989.

Primary Examiner—Eggerton A. Campbell
Attorney, Agent, or Firm—Burns, Doane, Swecker & Mathis, L.L.P.

[57] ABSTRACT

A novel gene, AF1q, is described and its cDNA sequence provided. Methods are provided for detection of malignancies in humans by examining the level of expression of or the integrity of the AF1q gene.

5 Claims, 10 Drawing Sheets

BamHI digestion
FIG. 1A

HindIII digestion
FIG. 1B

FIG. 2A

FIG. 2B cDNA sequence of AF1q:

```
AGTCAGCACG GGGGTGCTGG AAGAGATCGG GAATAATAGC GCAGACCAAT   50
GAGCCTAGGG AGATGCTTTC ATCGTCTCTC CTTCCCTCAA GTGTTCTGGA  100
ACCTATCATT TGAATTAGCC GAGTCAGGCA GGAGGGGGCG GGGAATCCTT  150
CCGCCCTTCT TAGGAGGGGC TGCATTGCAG GGGGAGAGTG AACTGACAGA  200
CTCAGTCACT GAAGAGGGAA AAGGAGTGAG AAGACAAAGC CGTCAAAGCC  250
CCAACAGCTT GTATTTCTCC AGCCCGGGGC AGACCCCGGA GCTCCCGAGG  300
CACTCCCTCC ATCTTTGGAA CACGCCAGTA ATTGATTGAT AACAGGAAGC  350
```

```
TATGAGGGAC CCTGTGAGTA GCCAGTACAG TTCCTTTCTT TTCTGGAGGA  400
  M  R  D   P  V  S  S   Q  Y  S   S  F  L   F  W  R  M
TGCCCATCCC AGAACTGGAT CTGTCGGAGC TGGAAGGCCT GGGTCTGTCA  450
  P  I  P   E  L  D   L  S  E  L   E  G  L   G  L  S
GATACAGCCA CCTACAAGGT CAAAGACAGC AGCGTTGGCA AAATGATCGG  500
D  T  A  T   Y  K  V   K  D  S   S  V  G  K   M  I  G
GCAAGCAACT GCAGCAGACC AGGAGAAAAA CCCTGAACGT GATGGCCTCC  550
 Q  A  T   A  A  D  Q   E  K  N   P  E  R   D  G  L  L
TTGAGTACAG CACCTTCAAC TTCTGGAGAG CTCCCATTGC CAGCATCCAC  600
  E  Y  S   T  F  N   F  W  R  A   P  I  A   S  I  H
TCCTTCGAAC TGGACTTGCT CTAAGGCCAA GACTTCTCTC TCCCATCACC  650
 S  F  E  L   D  L  L   X
TTGCCCTCAT TGTCTTCCCT CTCAAGCCCC TTCCTTTCCA CTCCTTTCCC  700
ATTTTAATCT TGTTCTCTCC CTACTGTGTT GGTGGTGCTG ATGAATCTGC  750
CAGAGTTGAG TTCTATGTAT TTATTTATCT ATCTGTCTAC TCCATTTCTC  800
TCAAAAGCCC TCAAGTCACA AAGTAAATGG TTCAAGCAAT GGAGTACTGG  850
GTCACAGGGA TTCCTCCTTT CCCCCCCAAA TATTAACTCC AGAAACTAGG  900
CCTGACTGGG GACACCTGAG AGTAGTATAG TAGTGCAAAA TGGAAGACTG  950
ATTTTTGACT CTATTATAAT CAGCTTCAGA GATTCCTTAA ACCTTCCTAA 1000
TTTCCTGCTC CAGGGCAGTA AACACAAATA TTTCTTCAAG GGGTGATGAA 1050
AACCTCGGAA GTTTTAATTT GAGGTTATCT GCTACGAAAC AGTATTTCTA 1100
AAAGGCTAAA GTGATAAGTC TCTTGCTTTT TTTTGATCCT GCTCTTATAT 1150
TCTTTTTTTT CCTCAGAGAA ATCAGGAGGG TAGTTAGAGG TATAAAACAG 1200
GAGGAAATAT TATGGAAAAT GAAATAGGG AAAATAATTG AATCATTTTA 1250
GAAGTAGCTA ATTTCTTTTC TCAAAAGAGT GTCCCTTCTT CACACCTACT 1300
CACTTTACAA CTTTGCTCCT AACTGTGGGT TGAAAACTCT AGCTAAAGAA 1350
AGTTATCAAA TCTTAACATG CATTCCTACT ATTATGATAG TTTTTAAGGT 1400
TTCAATTCAA TCTTCTGAAC GGCATAAGTC CTATTTTAGC CTTACCTCCT 1450
GCATTTGCAA TACGTAATAC TGATCAGTGG GCACAGTTCT TCAGCTACAT 1500
TGAGACCCTG AAATGAACAA TTATATTCTG ACTCGACATC TTGTCCCCAA 1550
TCCTTCCAAA AATATTGATG GTGATTTGTG CTACCATTTA CTCGTTTATT 1600
TaataaaGAC ATTCAATTCC CAAAAAAAA                         1629
```

FIG. 3

*In vitro* translation

FIG. 4

BamHI
FIG. 5A

XbaI
FIG. 5B

SEQUENCE OF AF1Q CDNA

This application claims priority from U.K. Application No. 9501386.8, filed Jan. 23, 1995.

This invention relates to a new cDNA sequence from the AF1q gene and to methods for cancer detection and therapy.

BACKGROUND OF THE INVENTION

Specific chromosomal translocations play an important role in oncogenesis of various malignancies including distinct types of hematopoietic malignancies[1]. Chromosomal translocations lead to malignancy mainly by one of two mechanisms. The first is transcriptional activation of a putative oncogene. This mechanism has been documented in many lymphoid malignancies where T cell receptor and immunoglobulin genes participate in various translocations. Activation of the oncogenic potential in these cases is the result of juxtaposing regulatory elements of T cell receptor and immunoglobulin genes near an oncogene causing transcriptional activation[2]. The second mechanism is the generation of transforming fusion products.

Chromosomal translocations involving the 11q23 region belong to the second category. However, this region is unique in that it is involved in translocations with several other chromosomal loci resulting in various types of leukemias[3–5]. Frequent translocations of the 11q23 band have been described with at least 15 different chromosomal partners[5]. This chromosomal band is frequently rearranged in acute lymphoblastio (ALL), in acute myelamonocytic (AMMOL), acute monocytic (AMOL) and acute myeloid (AML) leukemias mostly in reciprocal exchanges with specific translocation partners. The tissue specificity of the leukemia depends very much on the particular gene translocated to the 11q23 locus. Thus, the t(4;11)(q21;q23), t(11;19) (q23;p13), t(11;x), (q23;q13) and 1(1;11) (p32;q23) are found in 10%, 2%, >1% and >1% of ALL, respectively[6]. Reciprocal translocation between 11q23 and chromosomal bands 9p22, 6q27, 2p21, 10p11, 17q25 and 19p13 are found in 5%–6% of AML while t(1;11) t(q21;q23) are found in AMOL[7].

Recently, the gene involved in the recurring 11q23 chromosomal translocations has been identified[8–10]. This gene, called ALL-1, HRX or MLL, encodes an unusually large protein of 3972 amino acids (431 kDa) that is homologous to *Drosophila trithorax*, a homeotic transcriptional regulatory[11]. The homology between MLL and trithorax extends over four putative zinc finger DNA binding domains. In addition, the human gene alone contains two other potential DNA binding domains. The first consists of three AT hooks motifs that are implicated in minor groove DNA binding, and the second, is a region homologous to mammalian DNA methyltransferases[12]. The translocation breakpoints in all cases studied are tightly clustered in a 9 kb DNA region that spans exons 5 to 10 of the MLL gene[9,13–16]. The translocation disrupts the MLL gene between the N terminal "AT hook" domains and methyltransferase putative DNA binding domains, and the C terminal zinc fingers motifs.

Six different translocated partners fused to the MLL gene have been molecularly identified to date; these include 4q21, 9p21-22, 19p13, 1p32, 6q27 and 17q25[9,10,15,17–19]. In addition, partial duplication of the MLL gene spanning exons 2–6 were found in AML patients with trisomy 11 or without any cytogenetic abnormalities in chromosome 11[20]. Comparison of the amino acid sequence of these six proteins involved in translocation fails to suggest a specific sequence requirement for the fusion partner of band q23. However, it seems that the fusion partners of MLL may have in common motifs involved in protein interactions. Four of these proteins, AF-4, AF-6, AF-9 and ENL, contain domains rich in serine and proline residues, while AP17 contains a leucine sipper motif. Three of these proteins, AF-4, AF-9 and ENL, contain a nuclear targeting motif as well as other characteristics often found in transcription factors, while the other two, AP-6 and AF-1p, are homologous to cytoskeletal or cytoplasmic proteins involved in signal transduction. Thus, these motifs may act by altering the specific interaction regulating the multifunctional transcription activation by MLL and thus contribute to its oncogenic activity.

DESCRIPTION OF DRAWINGS

Certain embodiments of the invention are described, reference being made to the accompanying drawings, wherein:

FIG. 3 shows the nucleotide sequence of the AF1q cDNA (SEQ ID NO.2) and predicted amino acid sequence (SEQ ID NO.1). The fusion point with MLL in patient S is shown by arrow. ATTTA sequences and other AT-rich sequences involved in mRNA degradation are underlined. The polyadenylation signal is italicized.

B. relative levels of AF1q mRNA calculated from densitometry of three individual RT-PCR experiments and normalized according to β-actin expression.

Lanes (from left to right) contain 10 μg total RNA of the following cells: five pre-B leukemic call lines; HYOON, HOON, NALm6, B1, G2; T leukemic call line MOLT4; tRNA control RNA; undigested probe control; primary human fibroblasts; MOLT13 T calls; normal bone marrow stromal calls; normal bone marrow mononuclear cells; normal thymocytes; enriched population of normal CD4CD8 double positive thymocytes; human tonsilar cells.

DESCRIPTION OF THE INVENTION

The present inventors have identified a novel gene, AF1q, on chromosomal band Iq21 and have cloned its cDNA. The AF1q gene has been shown to be the fusion partner of the MLL gene in the t(1;11) (q21;q23) translocation in infants with acute myelomonocytic leukemia (AMMOL).

Chromosomal translocations involving band 11q23 have been described in various hematopoietic malignancies including acute leukemias (monocytic, myelomonocytic, lymphoblastic, mixed, or undifferentiated)[5]. one of the most striking features of 11q23 translocations is the multitude of chromosomal partners (at least 15) involved in reciprocal translocations with the MLL locus[5]. Typically, each of these translocations results in a specific leukemic phenotype, for instance, patients with t(4;11) characteristically present with biphenotypic ALL/AML, while patients with t(9;11), t(6;11), and t(11;17) present with AML[6,7].

To date, six of the translocation partner genes of the 11q23 have been cloned; these include 4q21, 9p21-22, 19p13, 1p32, 6q27 and 17q25[9,10,15,17,18,19]. In each of these cases, the creation of two reciprocal fusion proteins is predicted. The results of these molecular analyses suggest that interruption of the structure of the putative transcription factor MLL, and the formation of fusion proteins, alters its specificity and contributes to the uncontrolled growth that results in leukemia.

The inventors have cloned the t(1;11)(q21;q23) translocations from a patient with AMMOL. The involvement of the MLL gene was demonstrated at the molecular level in leukemic cells from this patient. The genomic breakpoint from leukemic cells of a patient with t(1;11)(q21-q23) was cloned using a probe within the breakpoint cluster of the MLL gene. Using a repeat-free chromosome 1 probe, the AP1q cDNA involved in the t(1;11)(q21;q23) was cloned. Chimeric MLL cDNA was isolated by PCR from one of these patients and was shown to contain chromosome band 1q21-derived sequences. Sequence analyses of the genomic breakpoints and of the fusion cDNA products predicted the creation of an in-frame fusion protein in derivative 11, but not in der(1), in leukemic cells from this patient. Sequence analysis of the AF1q cDNA predicted a protein of 90 amino acids. The AF1q mRNA is expressed in a number of tissues including high levels in the thymus while none of the mature hematopoistic cells at the periphery expresses AF1q mRNA. In contrast, AF1q mRNA is expressed in all hematopoietic tumors tested regardless of their degree of differentiation.

The molecular analysis of the t(1; 11)(q21;q23) helps clarify some of the questions regarding the oncogenic mechanisms of the translocations involving the MLL gene. The molecular evidence obtained by the inventors suggests which one of the two fusion MLL derivatives is the oncogenic product. This evidence comes from analysis of the t(1;11) (q21;q23) in an AMMOL patient that predicts the formation of only one fusion protein, that of der(11). The reciprocal derivative in this translocation not only lacks a fusion product, but also results in loss of the open reading frame of the carboxy terminal part of the translocated MLL gene. These data suggest that the N terminal part of the MLL gene containing the putative "AT hooks" DNA binding motifs and the DNA methyltransferase motif is the oncogenic part of the molecule. This prediction is consistent with previous evidence based on cytogenetic data[11,23].

The prediction that the N terminal portion of MLL is the oncogenic protein also suggests that the fused MLL uses its own promoter for expression in different types of leukemia. The differences in the phenotypic characteristics observed among leukemias with different fusion partners is thus likely due to structural differences contributed by the fusion partners rather than differential expression due to promoter elements.

The cDNA of AF1q encodes a small protein of predicted size of 90 amino acids as confirmed by in vitro translation. The predicted AF1q protein encoded by the cDNA has several interesting features. In addition to its unusually small size, AF1q has other features commonly found in nuclear oncogenes or cytokines, the presence of multiple mRNA destabilizing consensus sequences present in its untranslated 3' end[22] and the restricted and highly regulated expression of its mRNA in normal tissues but abnormal over-expression in tumour calls.

The following observations made by the inventors point to the AF1q gene as a putative common proto-oncogene: 1) an AF1q probe detected a rearrangement in a leukemic patient independent of the MLL fusion partner (FIGS. 1 and 5), suggesting that AF1q can cause cancer transformation independently of its fusion partner MLL; 2) overexpression of AF1q mRNA was seen in 8/13 cases of various types of hematopoietic malignancies (FIG. 9), suggesting that increased expression of AF1q is a common contributor to leukemic transformations (overexpression is defined as >10 fold than thymocytes which express the highest level of AP1q mRNA of all normal tissues); 3) tissue distribution of AF1q mRNA indicated exclusive expression in highly proliferative tissues such as thymus, intestine and colon (FIG. 7), a common characteristic of many proto-oncogenes; 4) cell cycle expression of AF1q mRNA was highly regulated and limited to a sharp peak at the G1/S interface, a crucial point in the control of the cell division cycle that is often affected in various cancers; 5) AF1q mRNA contains multiple 3' AUUUA mRNA destabilization motifs that are characteristic of nuclear oncogenes and of cytokine mRNAs; 6) other fusion partners of MLL function as transcriptional transactivators, a class of proteins often represented in proto-oncogenes; and 7) the chromosomal band 1q,21, the locus of the AF1q gene, is frequently rearranged in various malignancies.

The present invention provides a basis for diagnostic testing for cancerous cells or tissues, either by detecting rearrangements or translocations of the AF1q gene or by detecting abnormal expression of the gene.

a) Detection of rearrangements at AF1q gene locus in cancer samples.

Figure 5A:
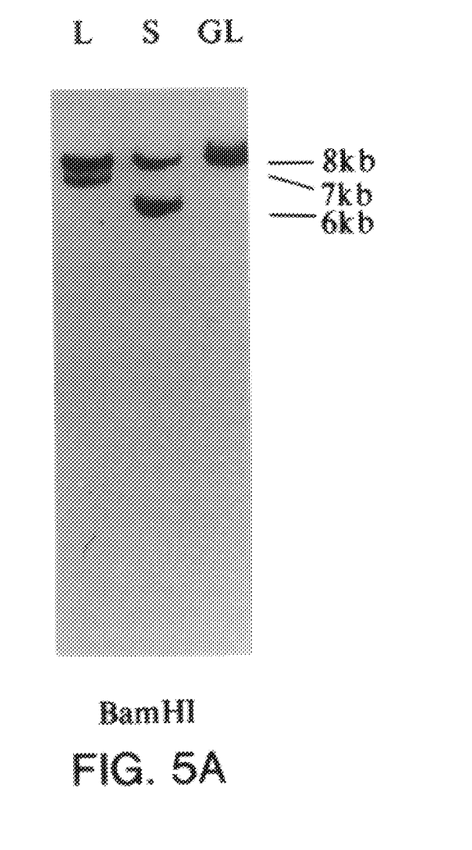
FIG. 5 shows a Southern blot analysis of two t(1;11) (q21;q23) patients using chromosome 1 probe. DNAs from two patients (L and S) with t(1;11)(q21;q23) and a normal control (GL) were digested with BamHI or XbaI and hybridized with the All chromosome 1 probe. The germ-line bands are 8 and 5 kb for BamHI and XbaI digestion respectively.
Figure 5B:
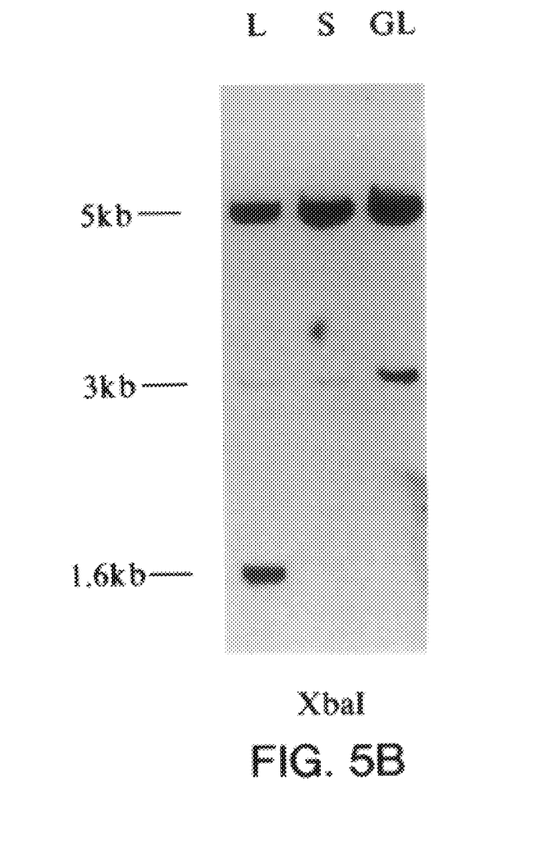
Figure 6:
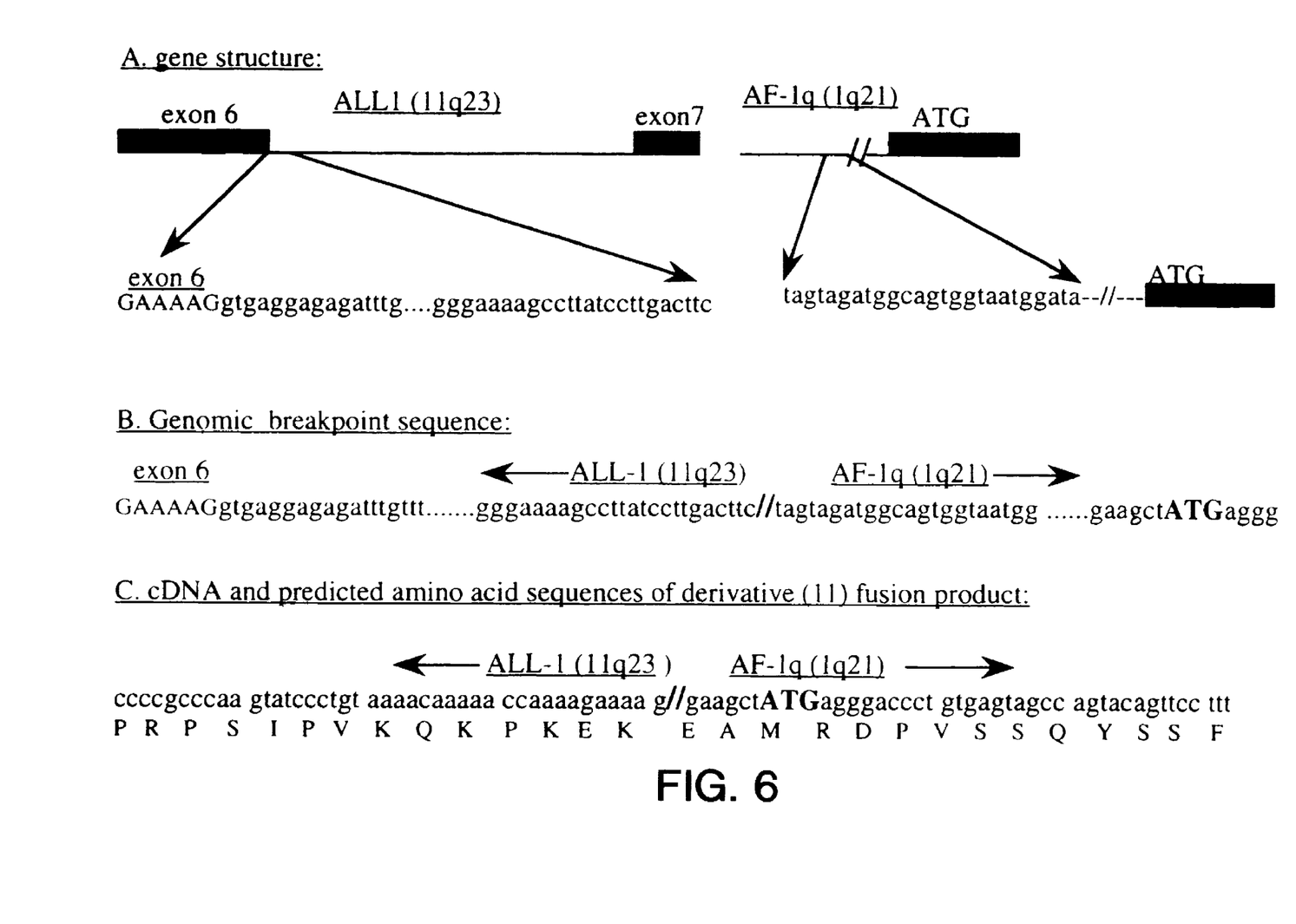
FIG. 6 shows a diagram of the genomic and cDNA fusion products in t(1;11) (q21;q23). A. Gene structure of the breakpoint region of MLL and AF1q. B. Genomic sequence of the breakpoint region of der (11) of patient S. C. cDNA fusion product of der(11) of patient S.

The AF1q cDNA sequences, genomic restriction enzyme maps, probes and oligonucleotide sequences of the invention can be used for the detection of various hematopoietic cancers (leukemias and lymphomas) and other types of cancer (carcinomas of the breast colon and lung etc.) as exemplified in FIGS. 5 and 6, as will be understood by those skilled in the art. The methods described in the examples herein can readily be adapted by those skilled in the art and applied diagnostically.

b) Detection of AF1q mRNA in cancer cells

Figure 7:
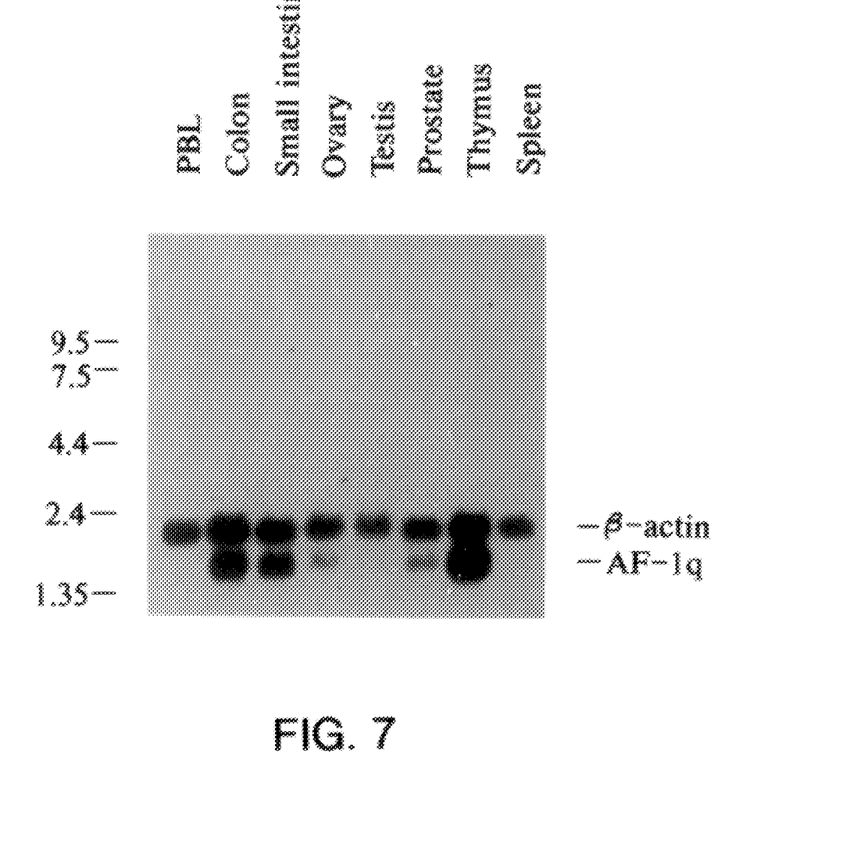
FIG. 7 shows Northern blot analysis of AF1q mRNA expression in various tissues. Hybridization with AF1q cDNA reveals 1.8 kb mRNA (lower band). Upper band was hybridized with β-actin probe.

High levels of expression of the AF1q mRNA were found in cancer cells (FIG. 9) but AF1q mRNA was completely absent in normal peripheral tissues (FIG. 7). The AF1q cDNA probes (FIGS. 7 and 9) and oligonucleotides (FIG. 8) of the invention permit the detection of AF1q mRNA in cancer cells by Northern analysis, RNAse protection, or polymerase chain reaction as described in the Examples and in FIGS. 7, 8 and 9, respectively.

As described in Example 3, the cDNA of the invention may be employed for in vitro production of the AF1q protein. Alternatively, the protein may be prepared in a suitable expression host, including bacteria, either as a separate protein or as a fusion protein. Polyclonal or monoclonal antibodies to the purified protein can be raised by standard techniques and can be employed in an immunoassay for the detection of AF1q protein in tissues or body fluids of patient for detection of various types of cancer as described above.

The sequence of the AF1q gene can be used to design oligonucleotides for gene targeting (gene therapy) to prevent expression of the corresponding mRNA in cancer calls, by methods previously described for other genes including oncogenes[28–30].

Furthermore, antibodies prepared to the AF1q protein may be employed to reduce or inhibit the is biological effect of the AF1q protein.

EXAMPLE 1

(a) Materials and Methods

Cell lines, freshly-isolated cells and tumour samples

The expression of AF1q mRNA was determined in various human cell lines from hamatopoietic tumours. The B1 cell line is a biphenotypic pre-B/myeloid call line from a leukemic patient with t(4;11)(q21;q23) established in our laboratory[25]. Other tumour cell lines, including the T lymphoblastoid line Jurkat, Molt 13, the promyleocytic cell line HL-60 and the monocytic cell line U937 were obtained from ATCC (Bethesda, Md.). Thymic tissue was obtained from samples removed from patients (1–4 years old) undergoing cardiac surgery at the Hospital for Sick Children and thymocytes were separated using Hypaque-Ficoll gradient centrifugation. Patient samples were obtained at diagnosis from bone marrow aspirations of two infants with AMMOL and >90% blast counts.

Southern and Northern blot Analysis

High molecular weight genomic DNA was extracted by standard procedures[26]. Cellular RNA was extracted after call disruption with guanidinium thiocyanate followed by phenol extraction[27]. DNA samples (10 μg) were size fractioned on 1.0% agarose gals. The denatured DNA was transferred to Hybond N membranes (Amersham). Hybridizations were carried out in 0.5M $NaH_2PO_4/Na_2PO_4$, 50% formamide, 1% SDS, 1 mM EDTA, with radiolabeled probes at 42° C. Northern analysis of multiple human tissues was carried out using human tissue mRNA blots obtained from Clontech (Palo Alto, Calif.).

cDNA and genomic cloning

The rearranged genomic fragments of MLL from patient DS with t(1;11)(q21;q23) were cloned into the EMBL-3 phage vector (Promega after partial digestion of the DNA with the Sau3A enzyme and size selection. The phage library was screened using a 0.9 kb BamHI fragment derived from the MLL cDNA spanning exons 5–11 (obtained from E. Canaani[9]). Fibroblast cDNA library was constructed using oligo (dT) priming cDNA kit (Stratogene, La Jolla, Calif.).

Figure 2A:
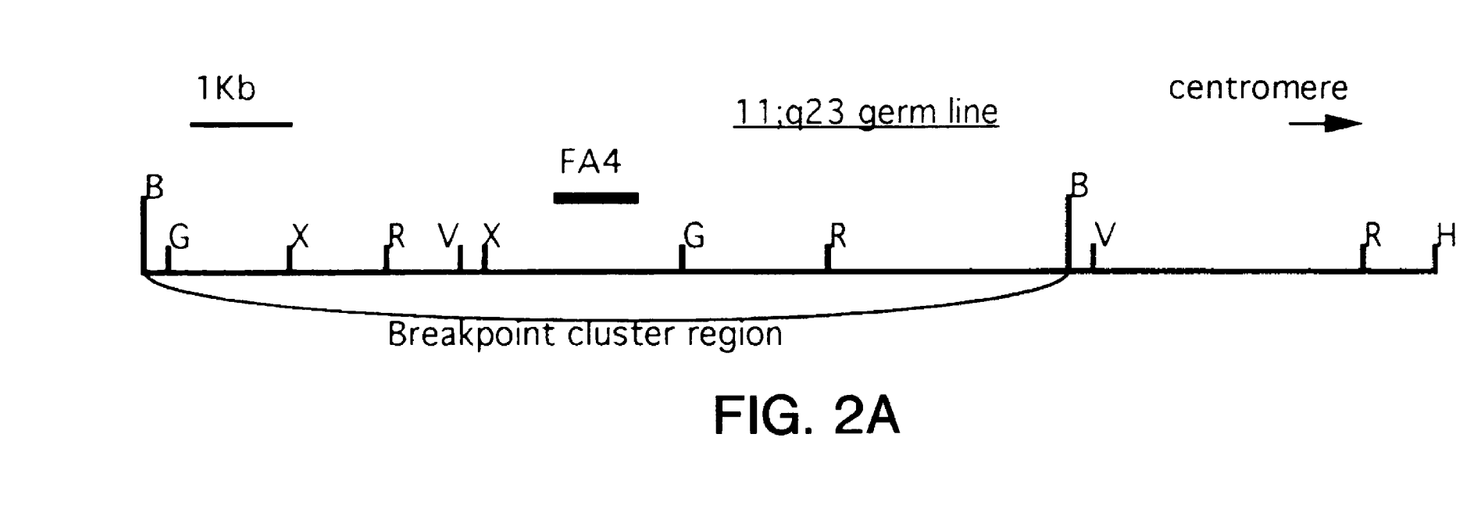
FIG. 2 shows genomic analysis of the t(1;11) (q21;q23) chromosome translocation. A. Physical map of the genomic junction of patient S [der(11)] and, B. A map of the corresponding normal region. Fragment All was used for screening of cDNA library. B, BamHI; R, EcoRI; H, HindIII; V, EcoRV; S, XbaI; G, BglII. The B859 cDNA probe used for Southern blot analysis covers the complete breakpoint cluster region included between the BamHI sites.
Figure 2B:
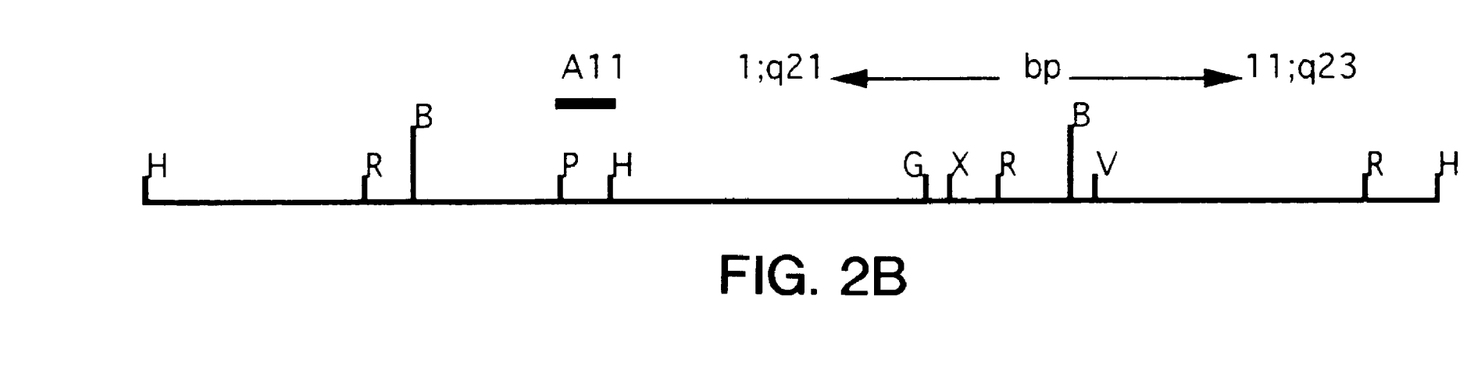

The cDNA library was screened using a repeat-free genomic fragment from the translocated chromosome 1 (labeled All in FIG. 2). Nucleotide sequencing of both strands was performed by the dideoxynucleotide method.

PCR procedures

RT-PCR was used for semi-quantitative measurements of the expression of AF1q gene in hemopoietic tissue and cells. First-strand cDNA was synthesized from total RNA, and used as PCR template. Thirty-six cycles were used for amplification of the AF1q cDNA and twenty-three cycles were used for amplification of actin cDNA. The PCR primers used for AF1q were: VT-1: (SEQ ID NO:4) 5' GGTGCTGGAAGAGATCGGGA; VT-2: (SEQ ID NO:5) 5' CAGTGACTGAGTCTGTCAGT, and for β-actin: Actin1: 5 ATCATGTTTAGACCTTCAA; Actin2: 5' CATCTCTTGCTCGAAGTCCA.

Figure 8A:
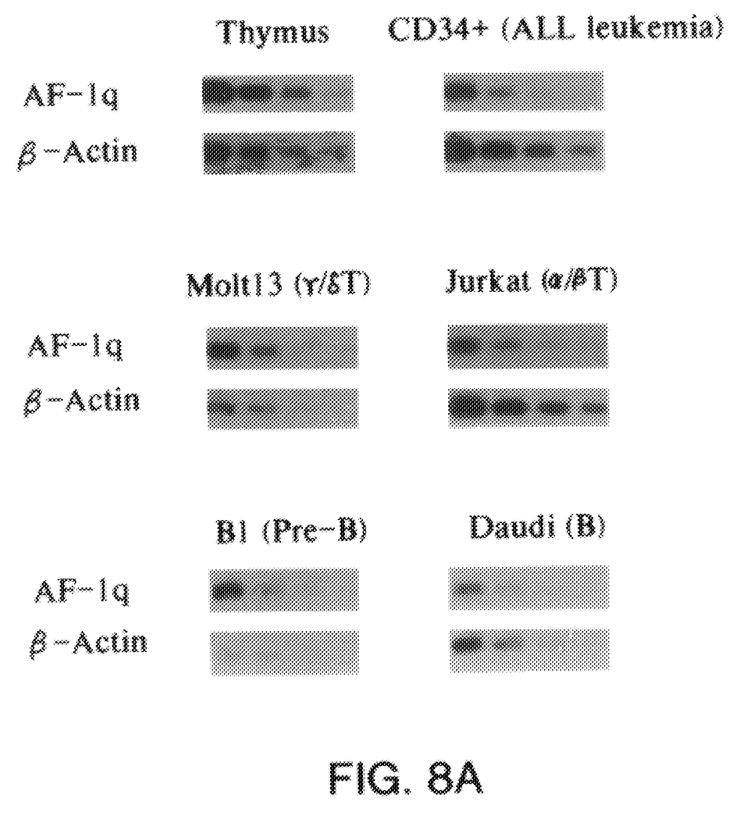
FIG. 8 shows RT-PCR analysis of the expression of AF1q mRNA in leukemic cells. A. 5.0, 2.5, 1.25 and 0.625 ng of total RNA were used (in respective lanes from left to right) for freshly-isolated thymocytes (thymus), CD34+ (AML) leukemic cells and Jurkat (leukemic T cell line). Ten-fold lower total RNA was used for amplification of cDNAs from B1 (ALL leukemic call line) and Molt13 cell (γδ leukemic cell line) and five times lower concentration of cDNA was used for Duadi cells. The PCR products were then run in 1.5% agarose gel, transferred to nylon membrane, and hybridized with 5'-labeled cDNA-specific deoxyoligonucleotides, (for AF1q PCR: TTCTTAG-GAGGGGCTGCATTGCAG and for β-actin: CTGGCATCGTGATGGACTCCGGTGAC).
Figure 8B:
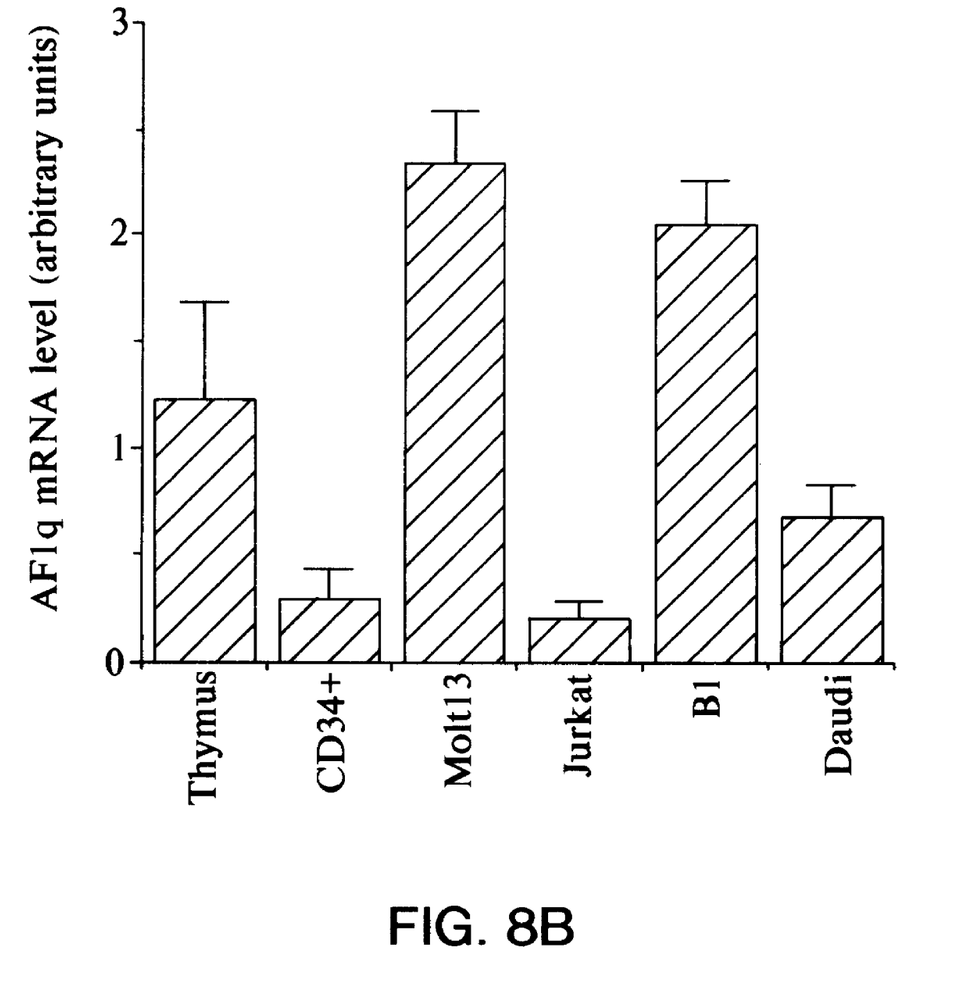

5.0, 2.5, 1.25 and 0.625 ng total RNA was used in each lane (from left to right) from thymocytes, CD34+ leukemic cells and Jurkat cells. Ten-fold lower total RNA was used for amplification of cDNAs from E1 and Molt13 cells and five times lower concentration of cDNA was used for Daudi cells. The PCR products were then run in 1.5% agarose gel in TAE buffer, transferred to nylon membrane, and hybridized with 5'-labeled cDNA-specific deoxyoligonucleotides, (for AF1q PCR; (SEQ ID NO:6) TTCTTAGGAGGGGCT-GCATGCAG and for β-actin: CTGGCATCGTGATGGACTCCGGTGAC), at 42° C. The membranes were washed with 2×SSC/0.1% SDS at room temperature and at 65° C. For the cloning of fused cDNA from a t(11;1)(q21;q23) patient: cDNA synthesis was performed using gene-specific primer. One μg total RNA was hybridized buffer (50% formamide/20 mM PIPES pH6.4/0.5 mM EDTA/0.2M NaCl) for 2 hours. First-strand cDNA was made from the hybrid by AVM-RTase at 42° C. for additional 2 hours. Negative controls PCR were routinely performed by eliminating the cDNA synthesis step, the lack of products in these reactions indicates the absence of genomic DNA contamination. PCR was carried out as described above using the following oligodeoxynucleotides: ALL1-5: 5'ATCAGAAGAGAGGATCCTGC (chromosome 11) and VT15-7: 5'GTCTGCTGCAGTTGCTTG (chromosome 1). PCR products were run in 1.5% agarose gel, transferred to nylon membrane, and hybridized to B859 (MLL cDNA fragment covering all known breakpoints) and VT15 (AF1q cDNA) probes. The PCR products were cloned in pCR II vector (Invitrogen) and screened with both B859 and VT15 probes. Positive clones were picked and sequenced.

(b) Involvement of the MLL gene in t(1;11)(q21;q23)

The MLL gene has been shown to be involved in the vast majority of leukemias with 11q23 abnormalities[16]. The inventors used Southern blot analysis to look for translocation at the MLL gene locus in two patients with t(1;11)(q21;q23). A genomic probe B859, which spans exons 5–11 of the MLL gene, detected a rearranged fragment in both BamHI and HindIII of DNA digests of one of these patients DNA. These data localized the presumed translocation in this patient within the breakpoint cluster of the MLL gene. No translocated fragment is detected in patient L consistent with previous reports of the existence of 11q23 translocations that involve the MLL gene but are outside the breakpoint cluster region[21].

Figure 1A:
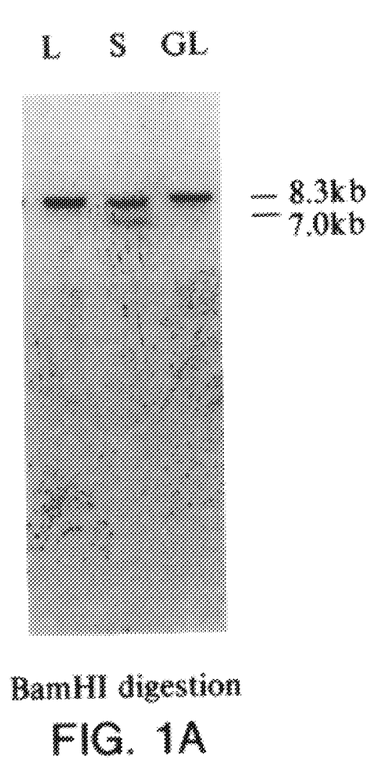
FIG. 1 shows a Southern blot of DNA from two patients with t(1;11) (q21;q23).
Figure 1B:
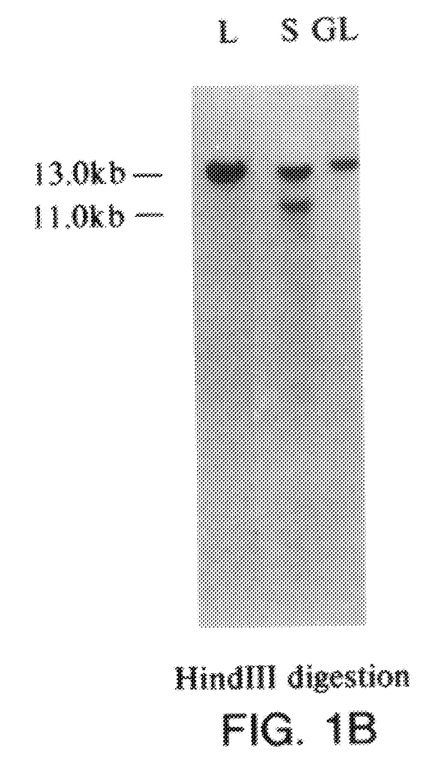

DNAs from leukemic cells of two patients (L and S) with t(1;11)(q21;q23) and a normal control (GL were digested with BamHI or HindIII and hybridized with the B859 probe. The germ-line bands are 8.3 and 13 kb for BamHI and HindHIII digestion respectively, patient S shows translocated bands of 7 and 11 kb which represent the gene involved in this translocation. The results are shown in FIG. 1.

EXAMPLE 2

Cloning of the 1q21 gene fused to MLL

Following the localization of the breakpoint in the MLL gene, we have used the B859 probe, spanning exons 5–11 of the MLL gene, to clone the genomic translocation for a t(1;11) (q21;q23) leukemic patient. DNA extracted from a bone marrow sample of this leukemic patient at diagnosis was used to construct a genomic library in the EMBL-3 λ phase. Out of $2\times10^6$ clones screened with this probe, eighteen positive clones were isolated. Restriction enzyme analysis of four of these clones identified a rearranged clone depicted in FIG. 2. The apparent breakpoint maps to the intron between exons six and seven.

EXAMPLE 3

Isolation of the AF1q cDNA

Using a repeat-free genomic DNA segment located 5 kb from the breakpoint on chromosome 1 (All in FIG. 2) a human fibroblast cDNA library was screened. Nine positive clones were isolated and both strands of the largest clones spanning 1.6 kb and 1.4 kb were sequenced. The sequence of the AF1q cDNA, presented in FIG. 3, contained 1644 nucleotides encompassing an open reading frame of 90 amino acids starting at nucleotide 401. There are stop codons in all frames upstream of the first ATG and a purine at the −3 position in accordance with the consensus for protein initiations. The 3' untranslated region is highly A+T rich (66%) and contained fifteen AT consensus motifs, including four ATTTA, which are commonly found in various cytokine genes and thought to destabilise highly regulated mRNA species[22]. An AATAAA polyadenylation signal starts at nucleotide 1602. The AF1q cDNA does not show any significant homology to any other sequence deposited in the GenBank.

Figure 4:
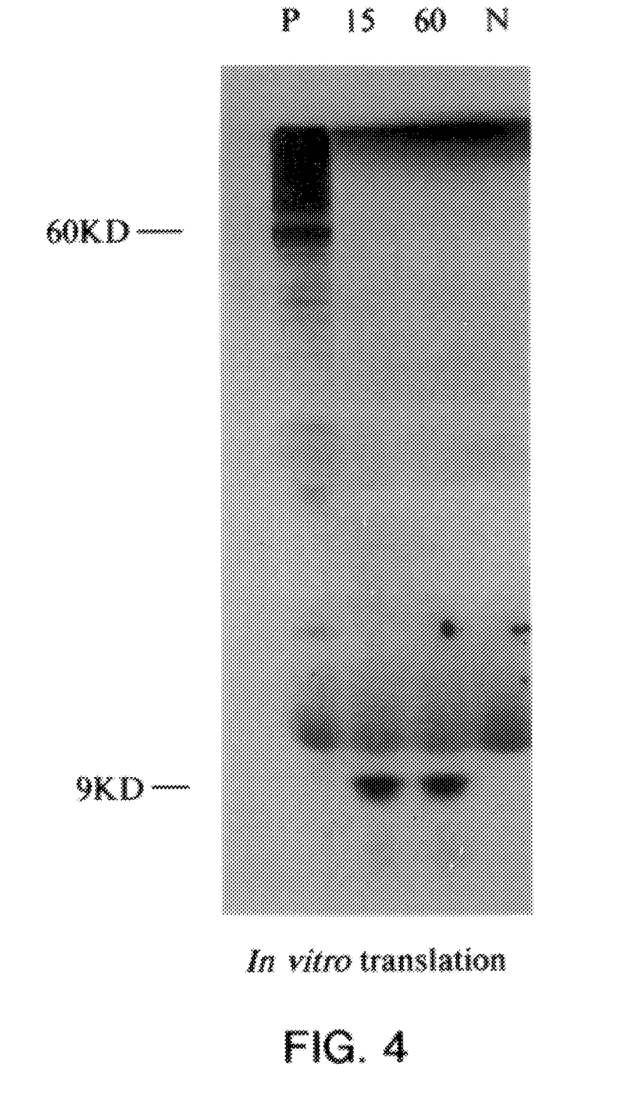
FIG. 4 shows in vitro translation of AF1q cDNA clones. T3-coupled reticulocyte lysate in vitro translation of two AF1q cDNA clones marked 15 (starting at nucleotide 350) and 60 (a full length cDNA clone) and a plasmid control (N).

To confirm the predicted open reading frame, two of the AF1q cDNA clones were translated using T3-coupled reticulocyte lysate in vitro translation system (FIG. 4). A single translation product was synthesized and its estimated size (9 Kd) is consistent with the deduced amino acid sequence of AF1q. Moreover, the involvement of the AF1q gene in t(1;11) (q21;q23) was further confirmed by using the cloned AF1q cDNA as a probe for the detection of rearranged bands in both BamHI and XbaI digests from a second infant with AMMOL (FIG. 5). These results confirm that the AF1q gene is in the proximity of the breakpoint cluster in two patients with t(1;11) (q21;q23).

The t(1;11)(q21;q23) breakpoint creates a fusion cDNA product of MLL/AF1q genes in an AMMOL patient Previous molecular analysis of six different chromosomal partners translocated to 11q23 always resulted in the formation of a fusion cDNA[9,10,15,17,18,19]. To examine whether this is also the case here, the inventors have used RT-PCR to determine the sequence of the MLL/AF1q fusion cDNA in the leukemic patient DS with t(1;11)(q21;q23). The results, depicted in FIG. 6, demonstrated that the translocation in der (11) creates a fusion cDNA between MLL and AF1q in this patient. The translocation breakpoint in chromosome 1 of patient S is particularly informative since it occurs six nucleotide upstream of the first ATG thus creating a predicted fusion protein of the MLL product with the entire AF1q cDNA in der(11) but in the reciprocal der(1) the open reading frame is destroyed and thus does not give rise to a protein product.

EXAMPLE 4

Expression of the AF1q mRNA

To examine the tissue distribution of AF1q mRNA, Northern blot analysis of poly(A)-selected mRNA from different tissues was carried out (FIG. 7). A single mRNA species of 1.8 kb was detected consistent with the longest cDNA clone isolated. AF1q mRNA is expressed in various tissues; it can be readily detected in colon and small intestine. Surprisingly, its expression in hematopoietic tissues is quite restricted. AF1q mRNA is abundant in the thymus, but is undetectable in peripheral hematopoietic tissues such as peripheral blood and spleen, suggesting that its expression is highly regulated during lymphocyte differentiation.

In light of the specific expression pattern in hematopoietic tissues, it was of interest to determine the expression of the AF1q mRNA in leukemic cells. RT-PCR was used to examine the relative expression or AF1q mRNA in leukemic cells of various lineages (FIG. 8). Despite its restricted expression in normal hematopoiesis to immature T cells, AF1q mRNA was expressed in all leukemic cells examined. Irrespective of their differentiation status, both lymphoid (B, pre-B and T calls), and myeloid (promyelocytic HL-60 cell line and monocytic cell line U937 (data not shown)), leukemic cells expressed AF1q mRNA at levels comparable to those found in thymocytes.

Figure 9:
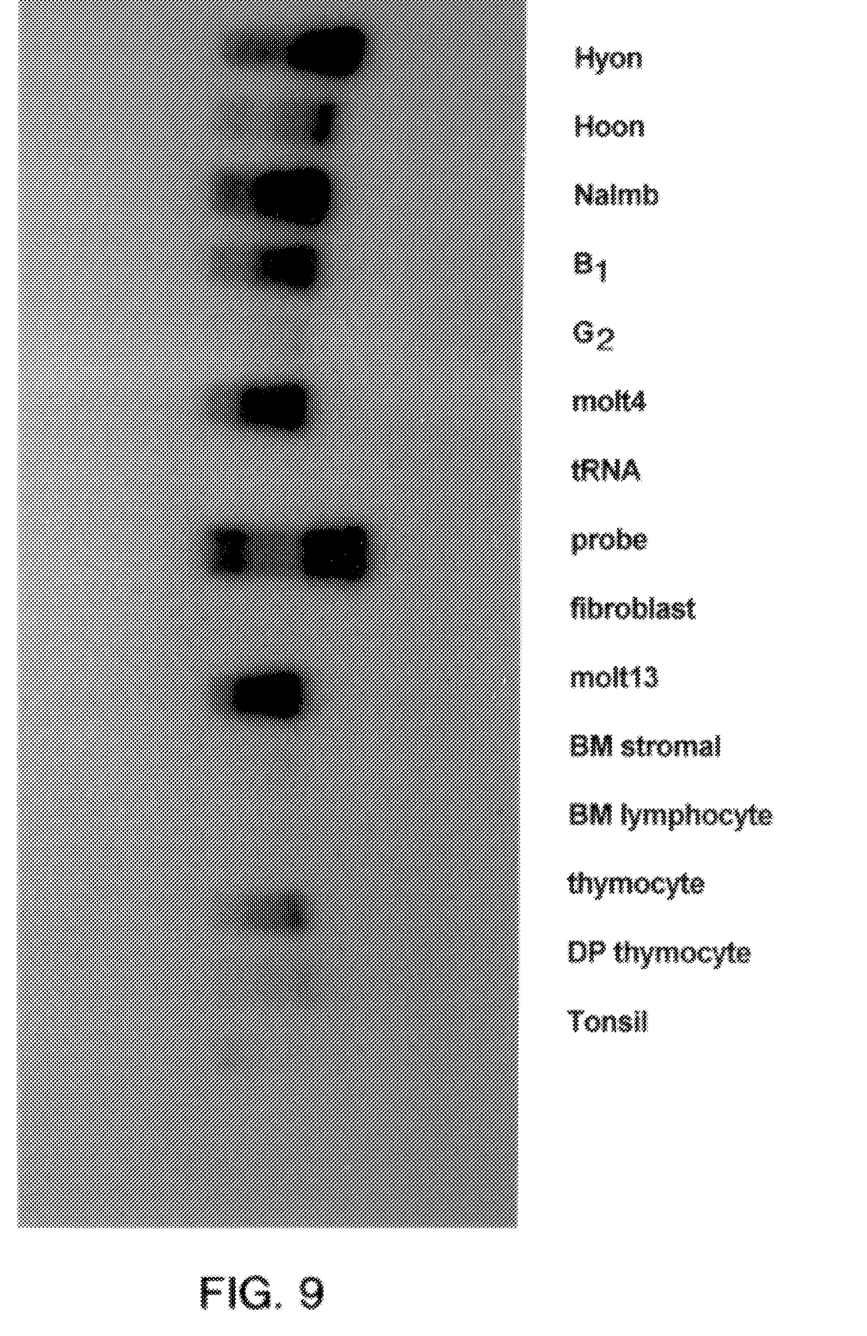
FIG. 9 shows expression of AF1q mRNA in normal human tissues and seven human leukemic cell lines.

In a further experiment, AF1q mRNA levels were analyzed in total RNA samples (10 μg/lane) from normal human tissues and from seven human leukemic call lines using RNAse protection assays. AF1q mRNA levels were overexpressed in five out of seven leukemic samples as compared to the levels in cells from normal tissues (leukemic cells expressed at least 10-fold higher levels of AF1q mRNA than thymocytes the highest AF1q expressing tissue). The results are shown in FIG. 9.

REFERENCES

1. Croce, C M: Role of chromosome translocations in human neoplasia. Cell 49:155–6, 1987
2. Gauwerky, C E and Croce, C M: Chromosomal translocations in leukaemia. Semin Cancer Biol 4:333–40, 1993
3. Kearney, L, Bower, M, Gibbons, B, Das, S, Chaplin, T, Nacheva, E, Chessells, J M, Reeves, B, Riley, J H, Lister, T A and et, al: Chromosome 11q23 translocations in both infant and adult acute leukemias are detected by in situ hybridization with a yeast artificial chromosome. Blood 80:1659–65, 1992
4. Petkovic, I, Konja, J and Nakic, M:. Cytogenetic analysis in children with acute nonlymphocytic leukemia. Cancer Genet Cytogenet 58:155–9, 1992
5. Young, B D: cytogenetic and molecular analysis of chromosome 11q23 abnormalities in leukaemia. Baillieres Clin Haematol 5:881–95, 1992
6. Pui Ching-Hon, C, W. M., Look A. T.: Biology and clinical significance of cytogenetic abnormalities in childhood acute lymphoblastic leukemia. Blood 76:1449–1463, 1990
7. Heim, S M, F.: Cancer Cytogenetics 1987
8. Djabali, M, Selleri, L, Parry, P, Bower, M, Young, B D and Evans, G A: A trithorax-like gene is interrupted by chromosome 11q23 translocationsin acute leukaemias. Nat Genet.2:113–8, 1992
9. Gu, Y, Nakamura, T, Alder, H, Prasad, R, Canaani, O, Cimino, G. Croce, C M and Canaani, E: The t(4;11) chromosome translocation of human acute leukemias fuses the ALL-1 gene, related to Drosophila trithorax, to the AF-4 gene. Cell 71:701–8, 1992

10. Tkachuk, D C, Kohler, S and Cleary, M L: Involvement of a homolog of Drosophila trithorax by 11q23 chromosomal translocations in acute leukemias. Cell 71:691–700, 1992

11. Harris, B N, Davis, E M, LeBaeau, M M, Bitter, M A, Kaminer, L S, Morgan, E and Rowley, J D; Variant translocations (;11): identification of the critical genetic rearrangement. Cancer Genet. 30:171–175, 1988

12. Ma, Q. Alder, H, Nelson, K K, Chatterjee, D, Gu, Y, Nakamura, T, Canaani, E, Croce, C M, Siracusa, L D and Buchberg, A M: Analysis of the murine All-1 gene reveals conserved domains with human ALL-1 and identifies a motif shared with DNA methyltransferases. Proc Natl Acad Sci U.S.A. 90:6350–4, 1993

13. Gu, Y, Alder, H, Nakamura, T, Schichman, S A, Prasad, R. Canaani, O, Saito, H, Croce, C M and Canaani, E: Sequence analysis of the breakpoint cluster region in the ALL-1 gene involved in acute leukemia. Cancer Res 54:2326–30, 1994

14. Hilden, J M, Chan, C S, Moore, R, Frestedt, J and Kersey, J R: Heterogeneity in MLL/AF-4 fusion messenger RNA detected by the polymerass chain reaction in t(4;11) acute leukemia. Cancer Res 53:3853–6, 1993

15. Nakamura, T, Alder, H, Gu, Y, Prasad, R, Canaani, O, Xamada, N, Gale, R P, Lange, B, Crist, W M, Nowell, P C and et, al: Genes on chromosomes 4, 9, and 19 involved in 11q23 abnormalities in acute leukemia share sequence homology and/or common motifs. Proc Natl Acad Sci U.S.A. 90:4631–5, 1993

16. Thirman, M J, Gill, H J, Burnett, R C, Mbangkollo, D, McCabe, N R, Kobayashi, H, Ziemin, vdPS, Kaneko, Y, Morgan, R, Sandberg, A A and et, al: Rearrangement of the MLL gene in acute lymphoblastic and acute myeloid leukemias with 11q23 chromosomal translocations, N Engl J Med 329:909–14, 1993

17. Domer, P, Fakharzadeh, S S Chen, C-S, Jockel, J, Johanson, L, Silverman, G A, Kersy, J H, Korsmeyer, S J: Acute mixed-lineage leukemia t(4;11)(q21;q23) generates an MLL-AF4 fusion product. Proc. Natl. Acad. Sci. U.S.A. 90:7884–7888, 1993

18. Bernard, O A, Mauchauffe, M, Mecucci, C, Van, dBH and Berger, R: A novel gene, AF-1p, fused to HRX in t(1;11)(p32;q23), is not related to AP-4, AF-9 nor ENL. Oncogene 9:1039–45, 1994

19. Prasad, R, Leshkowitz, D, Cu, Y, Alder, H, Nakamura, T, Saito, H, Hubner, K, Berger, R, Croce, C M and Canaani, E: Laucine-zipper dimerization motif encoded by the AF17 gene fused to ALL-1 (MLL) in acute leukemia. Proc. Natl. Acad. Sci. U.S.A. 91:8107–8111, 1994

20. Schichman, S A, Caigiuri, M A, Gu, Y. Strout, M P, Canaani, E, Bloomfield, C D and Croce, C M: All-1 partial duplication in acute leukemia. Proc. Natl. Acad. Sci. U.S.A. 91:6236–6239, 1994

21. McCabe, N R, Burnett, R C, Gill, H J, Thirman, M J, Mbangkollo, D, Kipiniak, M, van, ME, Ziemin, vdPS, Rowley, J D and Diaz, M O: Cloning of cDNAs of the MLL gene that detect DNA rearrangements and altered RNA transcripts in human leukemic calls with 11q23 translocations. Proc Natl Acad Sci U.S.A. 89:11794–8, 1992

22. Wilson, T and Treisman, R: Nature 336:396–399, 1988

23. Raimondi, S C, Peiper, S C, Kitchingman, G R, Behm, F G, Williams, D L, Hancock, M L and Nirro, J J: Childhood acute lymphoblastic leukemia with chromosomal breakpoints at 11q23. Blood 73:1627–34, 1989

24. Nagasawa, T, Kikutamni, H and Kishimoto, T: Molecular cloning and structure of a pre-B-cell growth-stimulating factor. Proc. Natl. Acad. Sci. U.S.A. 91:2305–2309, 1994

25. Cohen, A, Grunberger, T, Vanek, W, Dube, I D, Doherty, P J, Letarte, N, Roifman, C and Freedman, M H: Constitutive expression and role in growth regulation of interleukin-1 and multiple cytokine receptors in a biphenotypic leukemic cell line. Blood 78:94–102, 1991

26. Sambrook, J, Pritsch, E F and Maniatis, T: Molecular Cloning: A laboratory manual 2 vol edn. Cold Spring Harbor Laboratory Press, Cold Spring Harbor, N.Y. 1989

27. Chomczynaki, P and Sacchi, N: Single-step method of RNA isolation by acid guanidinium thiocyanate-phenol chloroform extraction. Anal. Biochem. 162:156, 1987

28. Ciardiello, F, Tortora, G, Bianco, C, Selvam, M P, Basolo, F, Fontanini, G. Pacifico, F, Normanno, N, Brandt, R. Persico, M G and et, al: Inhibition of CRIPTO expression and tumorigenicity in human colon cancer cells by antisense RNA and oligodeoxynucleotides. Oncogene 9:291–8, 1994

29. Manfredini, R, Grande, A, Tagliafico, E, Barbieri, D, Zucchini, P, Citro, G, Zupi, G, Franceschi, C, Torelli, U and Ferrari, S: Inhibition of c-fes expression by an antisense oligomer causes apoptosis of HL60 cells induced to granulocytic differentiation. Journal of Experimental Medicine 178:381–9, 1993

30. Perlaky, L, Saijo, Y, Busch, R K, Bennett, C F, Mirabelli, C K, Crooke, S T and Busch, H: Growth inhibition of human tumor cell lines by antisense oligonucleotides designed to inhibit p120 expression. Anti Cancer Drug Design 8:3–14, 1993

We claim:

1. An isolated DNA molecule comprising a nucleotide sequence encoding the amino acid sequence (Sequence ID NO:1) depicted in FIG. 3.

2. The DNA molecule of claim 1 wherein the nucleotide sequence comprises the nucleotide sequence depicted in FIG. 3 (Sequence ID NO:2).

3. The DNA molecule of claim 1 wherein the nucleotide sequence comprises nucleotides 352 to 621 of FIG. 3 (Sequence ID NO:3).

4. An isolated nucleic acid molecule comprising a nucleotide sequence selected from the group consisting of
   (a) a deoxyribonucleotide sequence complementary to Sequence ID NO:3;
   (b) a ribonucleotide sequence complementary to Sequence ID NO:3;
   (c) a nucleotide sequence complementary to the deoxyribonucleotide sequence of (a) or to the ribonucleotide sequence of (b);
   (d) a nucleotide sequence of at least 12 consecutive nucleotides capable of hybridizing to Sequence ID NO:3; and
   (e) a nucleotide sequence capable of hybridizing to a nucleotide sequence of (d).

5. An isolated DNA molecule comprising a nucleotide sequence SEQ ID NOS:6, 4 and 5, respectively selected from the group consisting of
   (a) TTCTTAGGAGGGGCTGCATTGCAG;
   (b) GGTGCTGGAAGAGATCGGGA;
   (c) CAGTGACTGAGTCTGTCAGT.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 90 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:1:

```
Met  Arg  Asp  Pro  Val  Ser  Ser  Gln  Tyr  Ser  Ser  Phe  Leu  Phe  Trp  Arg
1                   5                        10                       15

Met  Pro  Ile  Pro  Glu  Leu  Asp  Leu  Ser  Glu  Leu  Glu  Gly  Leu  Gly  Leu
               20                       25                       30

Ser  Asp  Thr  Ala  Thr  Tyr  Lys  Val  Lys  Asp  Ser  Ser  Val  Gly  Lys  Met
          35                       40                  45

Ile  Gly  Gln  Ala  Thr  Ala  Ala  Asp  Gln  Glu  Lys  Asn  Pro  Glu  Arg  Asp
          50                       55                  60

Gly  Leu  Leu  Glu  Tyr  Ser  Thr  Phe  Asn  Phe  Trp  Arg  Ala  Pro  Ile  Ala
65                       70                       75                            80

Ser  Ile  His  Ser  Phe  Glu  Leu  Asp  Leu  Leu
                    85                       90
```

(2) INFORMATION FOR SEQ ID NO:2:

(i) SEQUENCE CHARACTERISTICS:
        (A) LENGTH: 1629 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:2:

```
AGTCAGCACG  GGGGTGCTGG  AAGAGATCGG  GAATAATAGC  GCAGACCAAT  GAGCCTAGGG     60
AGATGCTTTC  ATCGTCTCTC  CTTCCCTCAA  GTGTTCTGGA  ACCTATCATT  TGAATTAGCC    120
GAGTCAGGCA  GGAGGGGGCG  GGGAATCCTT  CCGCCCTTCT  TAGGAGGGGC  TGCATTGCAG    180
GGGGAGAGTG  AACTGACAGA  CTCAGTCACT  GAAGAGGGAA  AAGGAGTGAG  AAGACAAAGC    240
CGTCAAAGCC  CCAACAGCTT  GTATTTCTCC  AGCCCGGGGC  AGACCCCGGA  GCTCCCGAGG    300
CACTCCCTCC  ATCTTTGGAA  CACGCCAGTA  ATTGATTGAT  AACAGGAAGC  TATGAGGGAC    360
CCTGTGAGTA  GCCAGTACAG  TTCCTTTCTT  TTCTGGAGGA  TGCCCATCCC  AGAACTGGAT    420
CTGTCGGAGC  TGGAAGGCCT  GGGTCTGTCA  GATACAGCCA  CCTACAAGGT  CAAAGACAGC    480
AGCGTTGGCA  AAATGATCGG  GCAAGCAACT  GCAGCAGACC  AGGAGAAAAA  CCCTGAACGT    540
GATGGCCTCC  TTGAGTACAG  CACCTTCAAC  TTCTGGAGAG  CTCCCATTGC  CAGCATCCAC    600
TCCTTCGAAC  TGGACTTGCT  CTAAGGCCAA  GACTTCTCTC  TCCCATCACC  TTGCCCTCAT    660
TGTCTTCCCT  CTCAAGCCCC  TTCCTTTCCA  CTCCTTTCCC  ATTTTAATCT  TGTTCTCTCC    720
CTACTGTGTT  GGTGGTGCTG  ATGAATCTGC  CAGAGTTGAG  TTCTATGTAT  TTATTTATCT    780
ATCTGTCTAC  TCCATTTCTC  TCAAAAGCCC  TCAAGTCACA  AAGTAAATGG  TTCAAGCAAT    840
GGAGTACTGG  GTCACAGGGA  TTCCTCCTTT  CCCCCCCAAA  TATTAACTCC  AGAAACTAGG    900
CCTGACTGGG  GACACCTGAG  AGTAGTATAG  TAGTGCAAAA  TGGAAGACTG  ATTTTTGACT    960
CTATTATAAT  CAGCTTCAGA  GATTCCTTAA  ACCTTCCTAA  TTTCCTGCTC  CAGGGCAGTA   1020
AACACAAATA  TTTCTTCAAG  GGGTGATGAA  AACCTCGGAA  GTTTTAATTT  GAGGTTATCT   1080
GCTACGAAAC  AGTATTTCTA  AAAGGCTAAA  GTGATAAGTC  TCTTGCTTTT  TTTTGATCCT   1140
GCTCTTATAT  TCTTTTTTTT  CCTCAGAGAA  ATCAGGAGGG  TAGTTAGAGG  TATAAAACAG   1200
GAGGAAATAT  TATGGAAAAT  GAAATAGGG   AAAATAATTG  AATCATTTTA  GAAGTAGCTA   1260
ATTTCTTTTC  TCAAAAGAGT  GTCCCTTCTT  CACACCTACT  CACTTTACAA  CTTTGCTCCT   1320
AACTGTGGGT  TGAAAACTCT  AGCTAAAGAA  AGTTATCAAA  TCTTAACATG  CATTCCTACT   1380
ATTATGATAG  TTTTTAAGGT  TTCAATTCAA  TCTTCTGAAC  GGCATAAGTC  CTATTTTAGC   1440
```

| | | | | | | |
|---|---|---|---|---|---|---|
| CTTACCTCCT | GCATTTGCAA | TACGTAATAC | TGATCAGTGG | GCACAGTTCT | TCAGCTACAT | 1500 |
| TGAGACCCTG | AAATGAACAA | TTATATTCTG | ACTCGACATC | TTGTCCCCAA | TCCTTCCAAA | 1560 |
| AATATTGATG | GTGATTTGTG | CTACCATTTA | CTCGTTTATT | TAATAAAGAC | ATTCAATTCC | 1620 |
| CAAAAAAA | | | | | | 1629 |

(2) INFORMATION FOR SEQ ID NO:3:

(i) SEQUENCE CHARACTERISTICS:
        (A) LENGTH: 270 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:3:

| | | | | | | |
|---|---|---|---|---|---|---|
| ATGAGGGACC | CTGTGAGTAG | CCAGTACAGT | TCCTTTCTTT | TCTGGAGGAT | GCCCATCCCA | 60 |
| GAACTGGATC | TGTCGGAGCT | GGAAGGCCTG | GGTCTGTCAG | ATACAGCCAC | CTACAAGGTC | 120 |
| AAAGACAGCA | GCGTTGGCAA | AATGATCGGG | CAAGCAACTG | CAGCAGACCA | GGAGAAAAC | 180 |
| CCTGAACGTG | ATGGCCTCCT | TGAGTACAGC | ACCTTCAACT | TCTGGAGAGC | TCCCATTGCC | 240 |
| AGCATCCACT | CCTTCGAACT | GGACTTGCTC | | | | 270 |

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:4:

| | | | |
|---|---|---|---|
| TTCTTAGGAG | GGGCTGCATT | GCAG | 24 |

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:5:

| | | |
|---|---|---|
| GGTGCTGGAA | GAGATCGGGA | 20 |

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "primer"

(xi) SEQUENCE DESCRIPTION: SEQ ID NO:6:

| | | |
|---|---|---|
| CAGTGACTGA | GTCTGTCAGT | 20 |